United States Patent [19]

Moro et al.

[11] Patent Number: 5,066,495

[45] Date of Patent: Nov. 19, 1991

[54] PROCESSES FOR THE PREPARATION OF PHARMACEUTICAL COMPOSITIONS CONTAINING BROMOCRIPTINE HAVING HIGH STABILITY AND RELATED PRODUCTS

[75] Inventors: Luigi Moro; Achille Fiori; Alberto Natali, all of Milan, Italy

[73] Assignee: Poli Industria Chimica S. P. A., Milano, Italy

[21] Appl. No.: 502,520

[22] Filed: Mar. 30, 1990

[30] Foreign Application Priority Data

Apr. 7, 1989 [IT] Italy ................................ 20063 A/89

[51] Int. Cl.⁵ ............................ A61K 9/48; A61K 9/20
[52] U.S. Cl. ...................................... 424/451; 424/79; 424/80; 424/452; 424/456; 424/464; 424/465; 424/489; 424/499

[58] Field of Search ............... 424/451, 452, 457, 464, 424/465, 8 D, 79, 489

[56] References Cited

U.S. PATENT DOCUMENTS

| | | | |
|---|---|---|---|
| 4,479,911 | 10/1984 | Fong | 424/497 |
| 4,615,881 | 10/1986 | Deibig et al. | 424/81 |
| 4,742,054 | 5/1988 | Naftchi | 424/449 |

*Primary Examiner*—Thurman K. Page
*Assistant Examiner*—James M. Spear
*Attorney, Agent, or Firm*—Walter H. Schneider

[57] ABSTRACT

Processes for the preparation of bromocriptine tablets or capsules wherein the active ingredient is protected by inclusion in an excipient or by separated granulation of the excipients and mixing granulate with a mixture of the active ingredient and a excipient having low moisture content.

8 Claims, No Drawings

PROCESSES FOR THE PREPARATION OF PHARMACEUTICAL COMPOSITIONS CONTAINING BROMOCRIPTINE HAVING HIGH STABILITY AND RELATED PRODUCTS

The present invention relates to methods for the preparation of tablets or capsules containing bromocriptine, which methods allow to obtain a product having remarkably higher stability characteristic than that of commercially available or traditional formulations.

The product prepared according to the methods of the present invention has the following advantages:
longer product shelf-life;
capability to be stored at higher temperatures than the one usually meant as "room temperature" and/or in not specifically protective packagings;
decreased content of any degradation products during the product shelf-life.

Bromocriptine is an alkaloid produced by fermentation from Claviceps purpurea and it has a characteristic dopaminergic action.

Bromocriptine is generally used in therapy as an antiprolactin agent, in the treatment of Parkinson's disease and in cocaine detoxication, in form of capsules or tablets.

Physico-chemical characteristics of bromocriptine require cautions in storage of the raw material: in fact, it is stored in tightly sealed containers, protected from light and moisture, in rooms having a temperature lower than 10° C. to prevent degradations, above all oxidations.

The sensitivity of the active substance to moisture, light and temperature conditions affects the related pharmaceutical formulations as regard both the preparation process and the product stability.

The most common product in the international market containing bromocriptine at a dosage of 2.5 and 1 mg consists of tablets known under the registered trade marks Parlodel and Pravidel. In the normal production of tablets, the techniques most known to those skilled in the art can be applied: mixing of the components and subsequent direct compression of the mixed powders, or granulation of a mixture consisting of active ingredient and excipients with a suitable binding solution and subsequent compression of the lubricated granulate.

These two techniques involve a different degree of exposure of the active ingredient to the above mentioned factors, which factors are able to promote its degradation: in fact, whereas direct compression of the mixed powder only exposes the drug to the residue moisture of the excipients, granulation, that is carried out with an aqueous solvent for security of the industrial environment, involves a momentary but remarkable localized increase of moisture, which is followed, however, by a drying period reducing the granulate water content to values even lower than the amount initially present in the excipients.

While both techniques involve exposure to the heat generated by compression, the granulation technique also involves exposure to the heat necessary for drying the granules, as well as a longer exposure to light because of a longer working time. On the other hand, granulation provides technological characteristics of the preparation (thickness, particle size and smoothness) which make compression easier.

Table 1 shows some accelerated stability data of two preparations having the same composition (bromocriptine mesylate 2.87 mg, maleic acid 2 mg, lactose 115.82 mg, maize starch 14 mg, PVP 4.2 mg, colloid silica 0.35 mg, stearate magnesium 0.7 mg), but prepared by means of the two above mentioned techniques: direct compression and wet granulation.

TABLE 1

Per cent daily amount of degradation products, bromocriptinine and other by-products, formed at the reported temperatures (calculated according to the slope of the regression line deriving from at least 3 pairs of values for each temperature).

| TEMPERATURE | USED PROCESS | |
|---|---|---|
| | Direct Compression | Wet Granulation |
| 60° C. | 1.686 | 0.833 |
| 50° C. | 0.366 | 0.125 |

From the above results it may be concluded that the behaviour under heat underlines the importance of moisture in the active principle degradation: in fact the product obtained by granulation, due to the drying to which it is subjected, shows a residual moisture content of 1.6%, whereas the one obtained by direct compression shows a residual water content of 2.5%. A careful analysis of the organoleptic characteristics of the tablets shows the importance of a homogeneous distribution in the final mixture of maleic acid, which is able to limit bromocriptine degradation but is also responsible for the darkening of tablets by reaction with the active substance.

The tablets prepared by direct compression show, after being exposed to high temperatures, a remarkable staining due to a not coarse but inevitable discontinuity of maleic acid distribution, whereas those prepared by wet granulation show a much more homogeneous darkening due to a more capillary distribution of maleic acid. Even better results are obtained with the tablets prepared according to the claimed methods, hereinbelow described.

It has now been found that pharmaceutical formulations having a good stability, in the form of both capsules and tablets, can be obtained by a preparation technique involving the incorporation of bromocriptine in an inert excipient that can effectively act as a barrier against the other substances that are present in the composition and against atmospheric agents, in particular against moisture. To this purpose, it is possible to use an excipient able to produce, after the contact with a not necessarily aqueous solvent, a remarkable swelling by expansion of its unitary volume promoted by solvation of the functional groups with which it is largely provided: if solvation is performed with a sufficiently concentrated bromocriptine solution, the subsequent desolvation phase, attainable by the traditionally known techniques, brings about a constriction in the excipient volume, that tends to incapsulate the active ingredient passed through the swollen structure during the previous swelling phase.

The main steps of said process can be summarized as follows:

1—dissolution of the active ingredient in a solvent or in a mixture of solvents able to produce a solution whose concentration of active ingredient is higher than 10% w/w;
2—use of the solution from step 1 to promote the swelling of an inert excipient unsoluble in the solvent or in the mixture of solvents;

3—drying of the mixture until reaching a residual solvent content lower than 1% and sieving through a suitable size net;

4—mixing of the powder from step 3 with the other components of the capsule or tablet formulation;

5—distribution of the powder mixture in unit doses (for capsules) or compression to unit weight (for tablets);

6—packaging in a container protecting against light and moisture.

Suitable solvents are ethyl alcohol, isopropyl alcohol, acetone, ethyl acetate, chloroform, methylene chloride, water, carbon tetrachloride, used individually or in admixture in any ratio.

Suitable swellable excipients are cross-linked PVP (trade name KOLLIDON CL or POLIPLASDONE XL), cross-linked sodium carboxymethyl cellulose, alginic acid and salts thereof, calcium carboxymethyl cellulose, starch and derivatives thereof, ion-exchanging resins (Amberlite IRP-64 ® and IRP-88 ®)

Thanks to the working procedure to which it is subjected, the active ingredient remains physically isolated from the other formulation excipients and from the atmospheric agents, with positive affects on the product stability.

The same object can be obtained by a preparation technique which is based on identical criteria of functional prevention and whose main points are the following:

1—use of the excipients that will get in contact with the active principle without further working processes in the form of anhydrous powders, or having a low residual moisture content;

2—use of a granulation phase on part of the excipient mixture with a binding solution that besides PVP can also contain maleic acid;

3—use of a forced drying process of the granulate until obtaining a residual water content lower than 1% w/w;

4—premixing of bromocriptine with part of lactose having a lower moisture content;

5—mixing the powders with the granulate containing maleic acid and addition of the lubricants;

6—compression of the mixed powder to granulate (for tablets) or distribution in gelatin capsules;

7—packaging in a container able to protect the formulation from light and moisture.

All the above operations are carried out under controlled moisture conditions and minimal variations around the 50% average value, as normal in rooms used for pharmaceutical production.

Such a preparation method allows to obtain a higher quality and stability of the pharmaceutical form since: as regards point 1, it prevents the active principle from the contact with the residual water contained in the excipients;

the step in which only of the excipients are granulated allows a homogeneous and regular distribution of the anti-oxidizing agent which is soluble in the solvent, as well as an improvement of the technological characteristics of the mass to be compressed, without exposing the active principle to the solvent of the binding solution and to the heat of a forced drying cycle;

the forced drying cycle to obtain a granulate having a moisture content lower than 1% allows to limit the residual solvent content of the tablet or the capsule within values conforming to those of the excipients;

premixture of the active ingredient, point 4, is necessary for the homogeneous distribution of the active ingredient which is present in the final mass in a very low percentage; as a support for the premix it is necessary to select a lactose with a very low residual moisture content;

mixing, distribution, compression and packaging, points 5, 6 and 7, are carried out according to the known technique and allow to obtain the final product in the form suitable for distribution and dispensation.

In particular, the packaging material plays a major role in keeping the initial organoleptic and chemico-physical characteristics of the tablets. What is reported above shows the advantages deriving from the use of a good material acting as a barrier against moisture and light affecting the product stability.

However, since in several countries, especially for the so-called "generic products", stocking is envisaged in big plastic bottles from which the prescribed amount of therapeutical unity has to be extracted and re-packaged, the product is required to keep its stability even when stored in packages that are not particularly protective. Results of 12 months of storage in such non protective conditions are listed in Table 2.

TABLE 2

| PRODUCT | BROMOCRIPTINE tablets | |
|---|---|---|
| STRENGTH | 2.5 mg | |
| BATCH NO. | 1038TF8 | |
| PACKAGING | HDPE bottles | |

| Characteristics | | initial | One yr. (Rm. Temp.) |
|---|---|---|---|
| Appearance | | white regular tablets | white regular tablets |
| Loss on drying | % | 1.59 | 1.04 |
| Disintegration time (min.) | min | 6.00 | 7.00 |
| Hardness | Kp | 6.00 | 6.00 |
| BROMOCRIPTINE m. content | mg/tab. | 2.55 | 2.44 |
| % vs. initial | % | 100.00 | 95.80 |
| BROMOCRIPTININE content | % | 0.00 | 0.55 |
| Degradation | % | 0.00 | 0.47 |
| Total degradation | % | 0.00 | 1.02 |

The product prepared according to the method of the present invention has, also in this case, a stability remarkably higher than that of the capsules prepared both by simple mixing and direct compression and with the traditional technique known to those skilled in the art, such as wet granulation of the active ingredient; moreover, the stability of the product according to the present invention turned out to be higher even to that of bromocriptine tablets at present available on the market, as shown by the results of the accelerated and stability tests reported in Table 3 below.

TABLE 3

Daily per cent amounts of degradation products, bromocriptinine and other by-products, formed at the reported temperatures (calculated according to the slope of the line deriving from at least 3 pairs of values for each temperature.)

| TEMPERATURE | Formulation according to the present invention (Lot n° 1038TF8) | | Commercial formulation (Lot n° 06/88-07) | |
|---|---|---|---|---|
| | packaging in glass bottle | packaging in blister | packaging in glass bottle | packaging in blister |
| 60° C. | 0.213 | 0.315 | 2.427 | 0.282 |
| 50° C. | 0.116 | 0.131 | 0.143 | 0.120 |
| 40° C. | n.d. | 0.0612 | n.d. | 0.083 |

Further to the substantial advantage of a higher stability of the product, the above processes described turn out to be advantageous also from an economic point of view, since in one case drying affects a fraction of the mass, thus allowing a remarkable energy saving in this working step, and in the other case there are no working losses of a very expensive active ingredient due to the steps of kneading, granulating and drying.

EXAMPLE 1

28.7 g of bromocriptine mesylate (equivalent to 25 g of bromocriptine base) were dissolved in 120 ml of 80% ethanol.

42 g of cross-linked polyvinylpyrrolidone were wet with the above solution, under stirring, thereafter they were dried under forced circulation of air heated to 60° C.

The powder was passed through a suitably sized net, before being admixed with 1,158.2 g lactose, 140 g starch, 20 g maleic acid, 3.5 g colloidal silicic acid and 7 g magnesium stearate until obtaining an homogeneous mixture which was pressed in unitary dosages weighing 140 mg, using 7 mm diameter plane punches, with breaking groove.

Tablets were obtained having a residual moisture content below 2% and a high disgregation rate, when placed into water at 37° C.

The blistered tablets show no signs of coloration nor darkening after 6 months storage at room temperature; the unblistered tablets kept in a glass container for 45 days at constant 60° C. show a very light darkening, which can hardly be noticed by comparison with tablets kept at room temperature and is definitely lower than darkening evidenced on tablets having the same qualitative-quantitative composition but prepared according to conventional techniques or mixing followed by direct compression and wet-granulation of a powder mixture containing the active ingredient.

EXAMPLE 2

28.7 g of bromocriptine mesylate (equivalent to 25 g of bromocriptine) were thoroughly mixed with 258.2 g of lactose, according to the progressive dilution technique and finally sieved through a 40 mesh net.

140 g of maize starch were separately admixed with 900 g of lactose; the mixture was kneaded with a PVP aqueous solution containing also maleic acid, which was forced through a suitably sized net, then dried at 50° C. to a residual moisture content lower than 1%, after which granulate was sieved through a suitably sized net.

The sieved granulate was combined with the mixture containing the active ingredient and with the lubricants before being subjected to compression on a rotary apparatus fitted with 7 mm diameter plane punches, provided with breaking groove.

Tablets were obtained of 140 mg unitary weight, having the following unitary composition:

| | |
|---|---|
| Bromocriptine methanesulfonate | 2.87 mg |
| maize starch | 14.0 mg |
| lactose | 115.82 mg |
| maleic acid | 2.0 mg |
| polyvinylpyrrolidone | 4.20 mg |
| colloidal silicic acid | 0.35 mg |
| magnesium stearate | 0.70 mg |

The resulting tablets showed the accelerated stability profile as in Table 2.

EXAMPLE 3

According to the procedure of Example 2, bromocriptine tablets having the following unitary composition were prepared:

| | |
|---|---|
| bromocriptine (equivalent to 1.0 mg base) | 1.147 mg |
| maize starch | 20.0 mg |
| lactose | 152.203 mg |
| maleic acid | 2.5 mg |
| polyvinylpyrrolidone | 2.4 mg |
| colloidal silicic acid | 0.45 mg |
| magnesium stearate | 1.3 mg |

The tablets have 180 mg average weight, a residual moisture content of 1.6% and disgregation time lower than 7 minutes.

The tablets passed the test for content uniformity with a per cent C.V. value of 2.43.

The accelerated stability profile of these tablets is very good: in fact, after 40 days at 50° C., they maintain the organoleptic characteristics nearly unchanged and show a 94.7% bromocriptine titre, a presence of bromocriptinine (a by-product still having pharmacological activity) lower than 5% and of other degradation products lower than 0.5%; after 1 month storage at 40° C. no degradation products different from bromocriptinine are noted, the latter being present in a very poor amount: 1.1%.

EXAMPLE 4

The powder mixture containing bromocriptine, obtained as described in Example 1, instead of being compressed is partitioned, at 280 mg unitary weight, into gelatin capsules, size 1, by means of a semi-automatic device. Capsules containing 5 mg of bromocriptine, as the base, are obtained, the content of which, after about 6 months at 30° C. constant temperature showed no signs of coloration of darkening.

EXAMPLE 5

28.7 g of bromocriptine mesylate (equivalent to 25 g of base) were thoroughly mixed with 258.2 g of lactose until homogeneous distribution of the active ingredient.

140 g of maize starch were separately mixed with 900 g of lactose and 20 g of maleic acid until obtaining an homogeneous distribution of the latter in the mixture, which was then kneaded with a binder solution containing 42 g of polyvinylpyrrolidone, dried at 50° C. to a solvent residual content lower than 1% and sieved through a suitably sized net.

Granulate, added with 3.5 g of colloidal silica and 7 g of magnesium stearate was compressed in unitary doses by means of a compressing device fitted with 7 mm diameter plane punches provided with breaking groove.

Tablets containing 2.5 mg of bromocriptine as the base were obtained, of 140 mg average weight, with a residual moisture content of 1.6% and having the following accelerated stability profile, for packaging in glass containers:

| Characteristics | Time 0 | After 30 days at 60° C. | After 6 months at 40° C. |
| --- | --- | --- | --- |
| Bromocriptine | 100.4% | 96.4% | 98.4% |
| Bromocriptinine | — | 3.3% | 2.3% |
| Others Degradations | — | 1.5% | 0.6% |

We claim:

1. A method for the preparation of a pharmaceutical composition in tablet or capsule form containing the active ingredient bromocriptine base or bromocriptine salified with organic or inorganic acids, which method comprises the following steps: (a) dissolving the active ingredient in a solvent or mixture of solvents capable of producing a solution having a concentration of active ingredient greater than about 10%, said solvent being selected from ethyl and isopropyl alcohol, acetone, ethyl acetate, chloroform, methylene chloride, water and carbon tetrachloride; (b) using the resultant solution to wet an excipient, or mixture of excipients, insoluble in said solution but subject to the swelling action thereof, said excipient being selected from cross-linked polyvinylpyrrolidone, cross-linked sodium carboxymethyl cellulose, calcium carboxymethyl cellulose, alginic acid and salts thereof, starch and derivatives thereof and ion exchange resins, whereby an expanded excipient is obtained; (c) drying said expanded excipient to produce an active ingredient-bearing excipient product having a residual moisture content of less than 1% and subjecting said product to separation; and (d) compressing said product into tablets or distributing it into capsules.

2. A method according to claim 1 in which additives to enhance the free flowing and lubricating characteristics of said product are added in step (d).

3. A method for the preparation of a pharmaceutical composition in tablet or capsule form containing the active ingredient bromocriptine base or bromocriptine salified with organic or inorganic acids, which method comprises the following steps: (a) preparing a mixture of the entire amount of active ingredient to be used in said composition with a portion of the total amount of a lactose to be used in said composition, said lactose being of very low residual moisture content; (b) preparing a granulate of the remaining lactose and an excipient, or mixture thereof, selected from cross-linked polyvinylpyrrolidone, cross-linked sodium carboxymethyl cellulose, calcium carboxymethyl cellulose, alginic acid and salts thereof, starch and derivatives thereof and ion exchange resins, with a solvent, or mixture of solvents, selected from ethyl and isopropyl alcohol, acetone, ethyl acetate, chloroform, methylene chloride, water and carbon tetrachloride; (c) drying said granulate to a residual moisture content of less than 1% and subjecting said granulate to separation; (d) forming a mixture of the product of step (a) and the granulate of step (c); and (e) compressing the mixture of step (d) into tablets or distributing it into capsules.

4. A method according to claim 3 in which maleic acid is added to the solvent of step (b) and additives to enhance the free flowing and lubricating characteristics of said mixture are added in step (d).

5. Tablets obtainable by the method as claimed in claims 4, containing as the active ingredient bromocriptine or the salts thereof in unitary doses from 0.5 mg to 25 mg calculated as the base.

6. Bromocriptine tablets according to claim 5, having the following unitary composition:

| | |
| --- | --- |
| Bromocriptine methanesulfonate (equivalent to 2.5 mg base) | 2.87 mg |
| maize starch | 14.0 mg |
| lactose | 115.82 mg |
| maleic acid | 2.0 mg |
| polyvinylpyrrolidone | 4.20 mg |
| colloidal silicic acid | 0.35 mg |
| magnesium stearate | 0.70 mg |

7. Bromocriptine tablets according to claim 5, having the following unitary composition:

| | |
| --- | --- |
| bromocriptine methanesulfonate (equivalent to 1.0 mg base) | 1.147 mg |
| maize starch | 20.0 mg |
| lactose | 152.203 mg |
| maleic acid | 2.5 mg |
| polyvinylpyrrolidone | 2.4 mg |
| colloidal silicic acid | 0.45 mg |
| magnesium stearate | 1.3 mg |

8. Capsules obtainable by the method as claimed in claims 1, containing as the active ingredient bromocriptine base or the salts thereof in unitary doses from 0.5 to 25 mg, calculated as the base.

* * * * *